United States Patent [19]

Wehner et al.

[11] Patent Number: 5,118,346
[45] Date of Patent: Jun. 2, 1992

[54] BIOCIDALLY ACTIVE COMPOUNDS

[75] Inventors: Wolfgang Wehner, Zwingenberg; Joachim Lorenz; Reinhardt Grade, both of Bensheim, all of Fed. Rep. of Germany

[73] Assignee: Ciba-Geigy Corporation, Ardsley, N.Y.

[21] Appl. No.: 644,868

[22] Filed: Jan. 23, 1991

Related U.S. Application Data

[63] Continuation of Ser. No. 590,460, Sep. 26, 1990, abandoned, which is a continuation of Ser. No. 508,518, Apr. 9, 1990, abandoned, which is a continuation of Ser. No. 317,318, Mar. 1, 1989, abandoned.

[30] Foreign Application Priority Data

Mar. 8, 1988 [CH] Switzerland .................. 862/88

[51] Int. Cl.$^5$ .................. C09D 5/16; C07F 9/02
[52] U.S. Cl. .................. 106/18.3; 106/18.31; 424/601; 568/9
[58] Field of Search .................. 106/18.3, 18.31; 424/601; 568/9

[56] References Cited

U.S. PATENT DOCUMENTS

| | | | |
|---|---|---|---|
| 4,038,197 | 7/1977 | Caspari | 252/46.7 |
| 4,874,526 | 10/1989 | Grade | 210/697 |
| 4,976,874 | 12/1990 | Gannoir et al. | 210/755 |

FOREIGN PATENT DOCUMENTS

| | | |
|---|---|---|
| 063327 | 10/1982 | European Pat. Off. |
| 1058618 | 3/1954 | France |
| 61-260259 | 11/1986 | Japan |
| 994881 | 6/1965 | United Kingdom |

OTHER PUBLICATIONS

Chem. Abstract 92: 25238w (1980).
Chem. Abst. 84: 75119p, 1976, Crivello.
Chem. Abst., vol. 106, 166193x (1987).
CA 107: 177897b.
CA 107: 15534d.
CA 107: 68042y.

Primary Examiner—William R. Dixon, Jr.
Assistant Examiner—Anthony J. Green
Attorney, Agent, or Firm—JoAnn Villamizar

[57] ABSTRACT

Compounds of the formula $$R^1{}_3Y^{\oplus} R^2 X^{\ominus} \quad (I)$$

in which the radicals $R^1$ are identical or different and are $C_2$–$C_6$ alkyl, phenyl, $C_1$–$C_2$ alkyl-substituted phenyl or $C_5$–$C_7$ cycloalkyl, benzyl, tolyl, or hydroxy-$C_1$–$C_4$ alkyl and $R^2$ is straight-chain or branched $C_8$–$C_2$ alkyl, and Y is P or N, or $R^1{}_3Y^{\oplus} R^2$ is

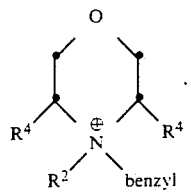

in which $R^4$ is H or —$CH_3$, or

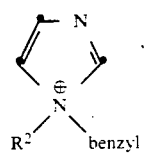

and X is $BF_4$ or $PF_6$, which are used as biocides, in particular in industrial solutions, in paints or in solid materials.

7 Claims, No Drawings

BIOCIDALLY ACTIVE COMPOUNDS

This application is a continuation of application Ser. No. 590,460, filed Sept. 26, 1990, now abandoned, which is a continuation of Ser. No. 508,518, filed Apr. 9, 1990, now abandoned, which in turn is a continuation of Ser. No. 317,318, filed Mar. 1, 1989, now abandoned.

The invention relates to novel biocidally active compounds of the quaternary ammonium and phosphonium base groups.

It is known from FR 1,058,618 that quaternary ammonium fluoborates, such as dodecyldimethylbenzylammonium fluoborate, can be applied to textile fibres as agents which prevent rot.

A compound of the type $N^{\oplus}Et_2$ benzyl $C_{12}H_{25}$ $PF_6^{\ominus}$ is known from JP 61-258,270 as a charge carrier for electrostatic image development.

GB 994,881 describes quaternary ammoniumfluoborates, for example n-alkyldimethylbenzylammoniumfluoborates, as catalysts for the manufacture of heatcuring resins.

Extremely active biocides with a broad biological action spectrum have now been found, suprisingly, from the series of quaternary ammonium and phosphonium bases as a cation in association with an anion from the group of the complex fluorine anions.

The present invention relates to compounds of the formula

  (I), in which the radicals $R^1$ are identical or different and are $C_2$–$C_6$alkyl, phenyl, $C_1$–$C_2$alkyl-substituted phenyl or $C_5$–$C_7$cycloalkyl, benzyl, tolyl or hydroxy-$C_1$–$C_4$alkyl and $R^2$ is straight-chain or branched $C_8$–$C_{22}$alkyl, and Y is P or N, or $R^1{}_3$ $Y^{\oplus}$ $R^2$ is

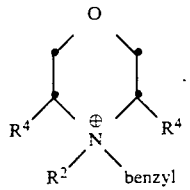

in which $R^4$ is —H or —$CH_3$, or

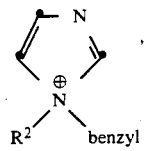

and X is $BF_4$ or $PF_6$, with the proviso, that $(C_2H_5)_2$(benzyl)$N^{\oplus}(C_{12}H_{25})PF_6^{\ominus}$ is excluded.

Compounds of the formula I in which $R^1$ is $C_3$–$C_6$alkyl and preferred is i-propyl, n-propyl, n-butyl or is phenyl, cyclohexyl, benzyl or hydroxyethyl are advantageous.

The invention preferably relates to compounds of the formula I in which Y is P and the radicals $R^1$ are identical or different and are i-propyl, n-butyl, phenyl or cyclohexyl, or Y is N and the radicals $R^1$ are identical or different and are n-propyl or n-butyl, or Y is N and the radicals $R^1$ are different and are 2-hydroxyethyl and benzyl, and $R^2$ is straight-chain or branched $C_8$–$C_{22}$alkyl, and X is $BF_4$ or $PF_6$.

In the compounds of the formula I, $R^2$ is a straight-chain or branched $C_8$–$C_{22}$alkyl radical and can be, for example, n-octyl, 2-ethylhexyl, 1-methylheptyl, 1,1,3-trimethylhexyl, decyl, undecyl, 1-methylundecyl, dodecyl, tridecyl, tetradecyl, pentadecyl, hexadecyl, heptadecyl, octadecyl, nonadecyl, eicosyl, henicosyl or docosyl. The alkyl radicals having 10 to 16 C atoms are advantageous, thus, for example, the decyl, undecyl, dodecyl, tridecyl, tetradecyl, pentadecyl and hexadecyl radicals, and alkyl radicals having 12 to 14 C atoms are preferred. The n-dodecyl radical and the n-tetradecyl radical can be regarded as particularly preferred.

Preferred compounds of the formula I according to the invention are those in which $R^1$ is n-butyl.

Other compounds of the formula (I) according to the invention preferably have the formula

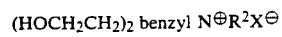

in which $R^2$ and X are as defined above.

In compounds of the formula (I) according to the invention, X is preferably $BF_4$.

Examples of compounds of the formula (I) according to the invention are:

(i-$C_3H_7$)$_3$ $Y^{\oplus}$ $R^2$ $X^{\ominus}$
(i-$C_3H_7$)$_2$ ($C_6H_5$) $Y^{\oplus}$ $R^2$ $X^{\ominus}$
(i-$C_3H_7$) ($C_6H_5$)$_2$ $Y^{\oplus}$ $R^2$ $X^{\ominus}$
(i-$C_4H_9$)$_3$ $Y^{\oplus}$ $R^2$ $X^{\ominus}$
(i-$C_4H_9$)$_2$ ($C_6H_5$) $Y^{\oplus}$ $R^2$ $X^{\ominus}$
(i-$C_4H_9$) ($C_6H_5$)$_2$ $Y^{\oplus}$ $R^2$ $X^{\ominus}$
(i-$C_3H_7$)$_2$ ($C_6H_5$) $Y^{\oplus}$ $R^2$ $X^{\ominus}$
(i-$C_4H_9$)$_2$ ($C_6H_5$) $Y^{\oplus}$ $R^2$ $X^{\ominus}$
(i-$C_4H_9$) ($C_6H_5$)$_2$ $Y^{\oplus}$ $R^2$ $X^{\ominus}$
($C_6H_5$)$_3$ $Y^{\oplus}$ $R^2$ $X^{\ominus}$
(n-$C_3H_7$)$_3$ $Y^{\oplus}$ $R^2$ $X^{\ominus}$
(n-$C_3H_7$)$_2$ (n-$C_4H_9$) $Y^{\oplus}$ $R^2$ $X^{\ominus}$
(n-$C_3H_7$) (n-$C_4H_9$)$_2$ $Y^{\oplus}$ $R^2$ $X^{\ominus}$
(n-$C_4H_9$)$_3$ $Y^{\oplus}$ $R^2$ $X^{\ominus}$ in which Y, $R^2$ and X are as defined above. Examples for preferred compounds are:

($C_2H_5$)$_3N^{\oplus}$($C_{10}$–$C_{14}$-Alkyl)$BF_4^{\ominus}$, the compound ($C_2H_5$)$_3N^{\oplus}$(n-$C_{14}H_{29}$)$BF_4^{\ominus}$ being particularly preferred,
(n-$C_3H_7$)$_3$ $N^{\oplus}$(n-$C_{14}H_{29}$)$BF_4^{\ominus}$,
(n-$C_4H_9$)$_3$ $P^{\oplus}$(n-$C_{14}H_{29}$) $PF_6^{\ominus}$,
($C_6H_5$)$_3$ $P^{\oplus}$(n-$C_{12}H_{25}$) $BF_4^{\ominus}$,
(n-$C_4H_9$)$_3$ $N^{\oplus}$(n-$C_{14}H_{29}$) $PF_6^{\ominus}$,
(n-$C_4H_9$)$_3$ $N^{\oplus}$(n-$C_{14}H_{29}$) $BF_4^{\ominus}$,
(HOCH$_2$CH$_2$)$_2$ (benzyl) $N^{\oplus}$(n-$C_{12}H_{25}$) $BF_4^{\ominus}$,

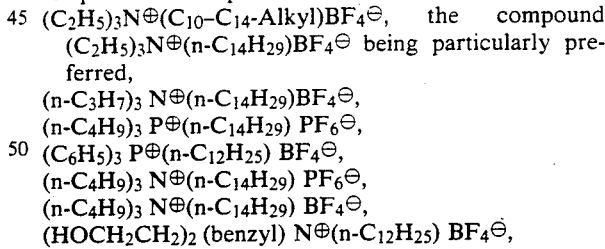

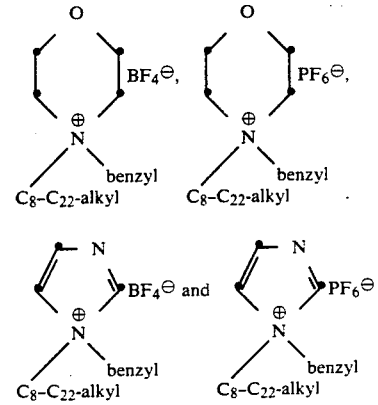

and, being particularly preferred, the compound of the formula $(n-C_4H_9)_3P^{\oplus}(n-C_{14}H_{29})BF_4^{\ominus}$.

The compounds according to the invention can be prepared in a manner known per se.

For example, corresponding ammonium and phosphonium halides are reacted with metal, for example alkali metal, or with ammonium fluoborates or phosphates to give the corresponding novel ammonium and phosphonium fluorine salts according to the invention.

For example, ammonium tetrafluoborate or lead tetrafluoborate or ammonium hexafluophosphate can be reacted with a quaternary ammonium or phosphonium halide $R^1_3YR^2$ Hal (Hal = halogen). The reaction conditions here are not critical and the reaction can be carried out, for example, under normal pressure at room temperature, and for example with water as the solvent.

The starting materials are likewise known per se and are in some cases commercially available products.

The compounds according to the invention are excellent biocides and have a broad biological action spectrum, so that they can be employed generally for industrial preservation of materials. In particular, they have an action against bacteria, fungi and algae, protozoa, molluscs, mussels, balanids, bryozoa, hydroids and the like.

The compounds of the formula I are therefore used according to the invention as biocides, in particular against the abovementioned organisms, for example as industrial biocides in the preservation of materials.

The compounds according to the invention are accordingly suitable—as preservatives for industrial solutions—as additives to building materials, preferably to mortars, plasters (interior plaster, exterior plaster, floor pavements and the like) or to mixtures containing hydraulic binders, such as concrete,—as additive to metal-working liquids, preferably to drilling and cutting oils, and furthermore also to rolling mill and forge separating and lubricating substances,—as additive to coating materials, advantageously to paints and varnishes, preferably to disperse dyes,—as an active medium in paint films for inhibiting or preventing rot, so-called anti-fouling paint films, for biocidal finishing of surface coatings generally and of wood, plastics, polymeric materials, paper, leather and textiles in particular—for surface treatment of or for incorporation into building materials and building elements of polymeric material,—as anti-slime agents in water systems, preferably in systems for cooling water and also preferably in industrial water, especially in the cellulose-processing industry, such as the paper industry, and finally—for disinfection.

A particularly preferred use of the compounds according to the invention is in anti-fouling paint films, and in this context particularly for paint films on objects immersed in seawater.

The compounds according to the invention are used in particular in all instances where objects which are to be protected from the growth of fungi and algae and attack by balanids, bryozoa, hydroids, molluscs, protozoa, mussels and bacteria are exposed to seawater. These are, in particular, hulls of ships, hydraulic structures, buoys and fishing nets, and also cooling and pipeline systems around or through which seawater flows. The compounds according to the invention generally protect all materials which may come into contact with seawater from growth or attack by the abovementioned organisms, for example wood, cellulose, textiles and leather, paints, varnishes, for example anti-fouling paints and similar coating materials, optical glasses and other glasses, plastics, rubber and adhesives, metals and mineral building materials, as well as other materials.

The compounds are employed in the concentration ranges known to the expert, depending on the intended use. The limits of the usable concentrations are given by the following values: whereas concentrations in the ppm range are already sufficient in cooling water, concentrations of up to 40% by weight are usual in anti-fouling formulations.

The compounds can be applied as dusting agents, scattering agents or misting agents in the pure form or together with carriers. They can also be dissolved or suspended in liquid media, and if appropriate, wetting agents or emulsifiers can promote uniform distribution of the active compound. Other biocides can be added.

A particularly preferred field of use is protective paints, in particular anti-fouling paints, which contain 0.5–40% by weight, preferably 3 to 15% by weight, based on the total mixture, of at least one compound of the formula I in addition to the customary base substances and additives.

The customary base substances for anti-fouling paints are the varnish raw materials which are called binders and are known to the expert, such as naturally occurring and synthetic resins, homo- and copolymeric products of the monomers vinyl chloride, vinylidene chloride, styrene, vinyl toluene, vinyl esters, vinyl alcohols and acrylic acid and methacrylic acid and esters thereof, polyester and polyamide resins, and furthermore chlorinated rubber, naturally occurring and synthetic rubber, which may be chlorinated or cyclized, and also casting resins, such as epoxy resins and polyurethane resins, and unsaturated polyesters, which, if appropriate, can be converted into film-forming higher molecular weight products by adding of curing agents.

The binders can be liquid or in dissolved form. In the case of dissolved binders, including thermoplastics, a protective film can also be formed by evaporating the solvent. Solid coating agents can be applied to objects, for example, by powder coating processes. Other customary base substances are, for example, tar, modifiers, dyes, inorganic or organic pigments, fillers and curing agents.

Finally, the compounds according to the invention can also be used in elastomeric coatings and in silicone elastomers and fluorine-containing polymers.

In practice, active compounds are frequently employed in combination with other biocides. The compounds according to the invention can also be combined with other biocides. Combinations of products often prove to be advantageous in anti-fouling paints. The compounds according to the invention can thus be used, for example, in combination with $Cu_2O$, CuSCN, zinc oxide, triorganotin compounds, such as tributyltin fluoride or triphenyltin chloride, metallic copper or triazines or generally with those compounds which are known to the expert as being active against animal or plant growth.

Another use form of the compounds according to the invention is incorporation into plastics or naturally occurring or synthetic rubbers, or application to surfaces of mouldings of these plastics, for example polyvinyl chlorides and copolymers and mixed polymers thereof, polyalkylenes, polyacrylates, polystyrenes, copolymers thereof, polyurethanes or polyisocyantes, polyesters, epoxy resins etc.

Use is particularly appropriate in plastics or polymeric materials which are used as building materials and, for example, are exposed to weathering, or are employed in the region of humid or wet areas. Examples which may be mentioned here are roofing materials or linings of polyvinyl chloride, butyl rubber, chlorinated polyethylene, polyisobutylene, chloroprene and chloroisoprene, EPDM and PVC copolymers with vinyl acetate or ethyl vinyl acetate, polyacrylonitrile-styrene, if appropriate mixed with fibrous fillers (if appropriate, also blended with bitumen), or foamed polyvinyl chlorides or polystyrenes, as insulating materials against heat and cold.

The compounds according to the invention are suitable both for the uses mentioned and for other uses. They are not hygroscopic, are stable to heat and have a very low water solubility.

The invention also relates to compositions containing at least one compound of the formula I according to the present invention. The form and nature of the particular composition containing the compound according to the invention depends on the intended use.

Compounds being preferred or being particularly preferred, as mentioned above, lead to compositions being preferred or being particularly preferred.

The compounds of the formula I can be in the following finished forms for application (the percentage by weight data in parentheses represent advantageous amounts of active compound):

Solid finished forms
Dusting agents and scattering agents (up to 10%). granules, coated granules, impregnated granules and homogeneous granules, pellets (grains) (1 to 80%).

Liquid finished forms
a) water-dispersible active compound concentrates: Wettable powders and pastes (25–90% in the commercial pack, 0.01 to 15% in the ready-to-use solution), emulsion and solution concentrates (10 to 50%; 0.01 to 15% in the ready-to-use solution);
b) Organic solutions (0.1 to 20%); aerosols.

The invention thus furthermore relates to agents containing the compounds according to the invention and to the use of the compounds and agents according to the invention for combating harmful organisms, for example bacteria, fungi, algae, protozoa, molluscs, mussels, balanids, bryozoa, hydroids and the like, in particular in the preservation of materials.

The biocidal agents according to the invention can also contain other active substances.

Examples of these are:
a) Organosulphur compounds, for example methylene dithiocyanate (MBT), isothiazolones or 3,5-dimethyl-tetrahydro-1,3,5-2H-thiodiazine-2-thione (DMTT). Such substances are used, in particular, against slime formation in papermaking.
b) Chlorinated phenols, such as sodium pentachlorophenolate. Such compounds are distinguished by a very broad action spectrum.
c) Copper salts, such as copper sulphate and copper nitrate as additional algicides.
d) 2,2-Dibromo-3-nitrilopropionamide (DBNPA) as an algicide, fungicide and bactericide.
e) Chlorine and bromine as algicides and bactericides, which are used in particular in water treatment.
f) Chlorine dioxide, chlorine isocyanurates and hypochlorites as biocides, for example in water treatment.
g) Triazines, for example 2-methylthio-4-t-butylamino-6-cyclopropylamino-s-triazine, in particular as algicides.
h) Triorganotin compounds, for example bis(tributyltin) oxide (TBTO), in particular as molluscicides, fungicides and algicides.
i) Wood biocide
  ia) Salt mixtures based on silicofluorides, hydrogenfluorides, inorganic boron compounds, chromates, fluorides, arsenic (oxide, arsenates), copper salts (sulphate, naphthenate), salts of tin and zinc and mercury compounds.
  ib) Tar oil preparations
  ic) Organic active compounds, such as pentachlorophenol, phenol, DDT, dieldrin, lindane, Gammexane, chlorinated naphthalenes, dichlofluanid, tributyltin compounds, pyrethroids, 3-iodo-2-propenyl N-butylcarbamate and furmecyclox.
j) Disinfectants
  ja) Phenol or phenol derivatives
  jb) Formaldehyde and/or other aldehydes and derivatives
  jc) Chlorine and organic or inorganic substances containing active chlorine
  jd) Amphotensides
  je) Quaternary onium compounds.

Of course, such formulations can moreover also contain other substances and auxiliaries, such as are usually co-used in such formulations. These include, for example, cationic or nonionic surface-active substances, electrolytes, complexing agents, solubilizing agents and dyes and fragrences. These additives are used, for example, for improving the wetting ability and curing stability, for adjusting the viscosity and for increasing the stability of the solutions to low temperatures.

When used in emulsion paints and plasters, the compounds according to the invention can be combined with another fungicide. Combinations with a bactericide are possible in water treatment, in order to combat slime-forming bacteria. Such combinations can bring technological advantages. In many cases combination with other algicides is also advantageous.

The invention also relates to compositions containing a) a paint and b) an effective amount of at least one compound of the formula (I) according to the present invention.

The following examples illustrate the invention in more detail without limiting its scope. Percentages (%) quoted therein are percentages by weight and parts are parts by weight.

EXAMPLES

1. Tri-n-butyl-n-tetradecylphosphonium tetrafluoborate 2,176 g of a 50% strength solution of tri-n-butyl-n-tetradecylphosphonium chloride in water are added dropwise to 314.5 g (3.0 mol) of ammonium tetrafluoborate in 5 of $H_2O$ at 2° C., with vigorous stirring, a thick precipitate forming. After the mixture has been left to settle for a short time, the precipitate is filtered off with suction, rinsed with 3 portions of 500 ml of water and dried to constant weight over $P_2O_5$.

Yield: 1,192 g, corresponding to 98% of theory— melting point: 39° C.

2. Tri-n-butyl-n-tetradecylphosphonium hexafluophosphate

The preparation is analogous to Example 1, except that an equivalent amount of a 50% strength aqueous ammoniumhexafluophosphate solution is used.

Yield: 80%—melting point: 41° C.

3. Triphenyl-n-dodecylphosphonium tetrafluoborate 5.5 g (0.00715 mol) of a 50% strength aqueous solution of lead tetrafluoborate are added to 22.3 g (0.0143 mol) of a 30% strength aqueous solution of triphenyl-n-dodecylphosphonium chloride, while stirring. The precipitate formed is digested with 250 ml of methanol, the lead chloride is filtered off and the methanolic solution is concentrated to a residue.

Yield: quantitative—yellow, highly viscous oil, $n_D^{20} = 1.5414$.

4. Tri-n-butyl-n-tetradecylammonium hexafluophosphate

A solution of 3.3 g (0.02 mol) of ammonium hexafluophosphate in 20 ml of water is added to a solution of 9.3 g (0.02 mol) of tri-n-butyl-n-tetradecylammonium bromide in 50 ml of water, while stirring. The precipitate formed is filtered off, washed and concentrated to a residue.

Yield: 85% of theory—melting point: 104° C.

5. Tri-n-butyl-n-tetradecylammonium tetrafluoborate 7.6 g (0.01 mol) of 50% strength lead tetrafluoborate solution are added to a solution of 9.3 g (0.02 mol) of tri-n-butyl-n-tetradecylammonium bromide in 50 ml of water, while stirring. The precipitate is decocted with isopropanol and the lead bromide is separated off. The filtrate is then concentrated to a residue.

Yield: 70%—melting point: 88° C.

6. Bis(hydroxyethyl)benzyl-n-dodecylammonium tetrafluoborate 16.8 g (0.16 mol) of ammonium tetrafluoborate in 200 ml of water are added to 49.5 g (0.124 mol) of bis(hydroxyethyl)benzyl-n-dodecylammonium chloride in 500 ml of water, while stirring, during which an oil separates out, which is taken up in 200 ml of ethyl acetate, the mixture being washed several times with water. After drying, the mixture is concentrated to a residue.

Yield: 95% of theory—pale yellow viscous oil, $n_D^{22} = 1.4812$.

EXAMPLE 7

Preparation of the Compounds of the Formula $[(C_2H_5)_3N(^nC_{12}H_{25})]^{\oplus}BF_4^{\ominus}$.

0.06 mol (6.3 g) of ammonium fluoborate in 100 ml of water is added dropwise to a solution of 0.06 mol (21.0 g) of triethyllaurylammonium bromide in 250 ml of water, while stirring. The precipitate formed is filtered off with suction, washed free from bromide and dried to constant weight.

Yield: 21.1 g (98.6% of theory)—melting point: 127°-128° C.

The following $N^{\oplus}BF_4^{\ominus}$ salts are obtained analogously to Example 7:

| Example | $N^{\oplus}$ | Yield [%] | Melting point [°C.] | Comments |
|---|---|---|---|---|
| 8 | $(C_2H_5)_3N(^nC_{14}H_{29})$ | 96.9 | 146–147 | |
| 9 | $(C_2H_5)_3N(^nC_{18}H_{37})$ | 93.7 | 168–171 | ammonium bromide dissolved in water/methanol*) |
| 10 | $(^nC_3H_7)_3N(^nC_{14}H_{29})$ | 93.5 | 69–70 | |
| 11 | $(C_2H_5)_3N(^nC_8H_{17})$ | 67.8 | 89–91 | the oil which separates is extracted with ethyl acetate and the extract is washed free from bromide and concentrated to a residue |
| 12 | $(C_2H_5)_3N(^nC_{10}H_{21})$ | 80.2 | 105–107 | precipitation is carried out at +3° C. |
| 13 | $(C_2H_5)_3N(^nC_{16}H_{33})$ | 91.3 | 160–161 | ammonium bromide dissolved in water/methanol*) |
| 14 | morpholinium with CH₂C₆H₅ and $^nC_{12}H_{25}$ substituents | 93.5 | 56–58 | ammonium bromide dissolved in water/methanol*) |
| 15 | imidazolinium with CH₂C₆H₅ and $^nC_{10}H_{21}$ substituents | 95.2 | viscous oil ($n_D^{20}$ = 1.4762) | ammonium bromide dissolved in water/methanol*), the oil which separates out is taken up in ethyl acetate and the mixture is washed free from bromide and concentrated to a residue. |

*) Just enough methanol is added to the aqueous suspension for a clear solution to result.

EXAMPLE 16

Determination of the Minimum Inhibitory Concentration against Bacteria

The ONCs (overnight-incubated cultures), washed in Caso peptone broth (Merck), of the various bacteria strains: A) *Proteus vulgaris*, B) *Pseudomonas aeruginosa*, C) *Enterobacter aerogenes*, D) *Serratia marcesens*, E) *Alcaligenes denitrificans* and F) *Bacillus subtilis*, are in each case diluted 1/1,000 in saline. An amount of the suspension is introduced into Caso peptone broth such that the bacteria are diluted again to 1/1,000. The compounds shown in Table 1 are then added in each case in amounts of 30, 100 and 300 mg/1. After incubation at 30° C. for 24 hours in a shaking water bath, the mixtures are evaluated according to their turbidity. The minimum inhibitory concentration (MIC) is the concentration at which the broth does not become turbid due to bacterial growth.

The results are illustrated in the following Table 1:

TABLE 1

| Determination of the MIC against bacteria (concentration in g/l) | | | | | | |
|---|---|---|---|---|---|---|
| Compound from example | Strain | | | | | |
| | A | B | C | D | E | F |
| 1 | 30 | 100 | 30 | 30 | 30 | 30 |
| 3 | 30 | 30 | 30 | 30 | 30 | 30 |
| 5 | 30 | 300 | 30 | 30 | 30 | 30 |
| 6 | 30 | 100 | 100 | 100 | 30 | 30 |
| 7 | 300 | >300 | >300 | 300 | >300 | 30 |
| 8 | 30 | 300 | 30 | 100 | 30 | 30 |
| 9 | 30 | >300 | >300 | >300 | >300 | 30 |
| 10 | 30 | >300 | 100 | 100 | 100 | 30 |
| 13 | 30 | >300 | 30 | 30 | 300 | 30 |
| 14 | 100 | 300 | 300 | 300 | 100 | 30 |
| 15 | 100 | 300 | 100 | 300 | 100 | 100 |

The good growth-inhibiting action of the compounds even against the Gram-negative bacteria which are difficult to combat can be seen from Table 1.

EXAMPLE 17

Determination of the Minimum Inhibitory Concentration (MIC) against Fungi

Strains: A) *Aspergillus niger*, B) *Sacharomyces cerevisiae*, C) *Penicillium funiculosum*, D) *Chaetomium globosum*, E) *Aureobasidium pullulans* and F) *Coniophora puteana*.

The investigation is carried out by the known agar incorporation test in malt extract agar (Merck). For the inhibition, the various compounds are in each case added in an amount such that concentrations of 10, 50 and 100 mg/l result in the agar. The concentrations (mg/l) required for inhibiting the growth of the fungi (starting from fungus spores dripped on) are illustrated in Table 2.

TABLE 2

| Determination of the MIC against fungi (concentration in mg/l) | | | | | | |
|---|---|---|---|---|---|---|
| Compound from example | Strain | | | | | |
| | A | B | C | D | E | F |
| 5 | 100 | 50 | 50 | 50 | 50 | 100 |
| 1 | 50 | 10 | 10 | 10 | 50 | 10 |
| 3 | 100 | 50 | 10 | 50 | 10 | 50 |
| 2 | 100 | 10 | 10 | 100 | 50 | 100 |
| 6 | >100 | 50 | 10 | 50 | 10 | 50 |
| 7 | >100 | >100 | 50 | 100 | 50 | 50 |
| 8 | 50 | 100 | 10 | 50 | 10 | 50 |
| 9 | >100 | >100 | 50 | 50 | 50 | 50 |
| 10 | 100 | 100 | 50 | 50 | 10 | 10 |
| 13 | 100 | 100 | 10 | 100 | 50 | 10 |
| 14 | >100 | >100 | 50 | 100 | 10 | 50 |
| 15 | >100 | 100 | 10 | 50 | 50 | 10 | concentration tested: 10, 50, 100 mg/l.

It can be seen from Table 2 that the compounds are also outstanding fungicides.

EXAMPLE 18

Use of the Compounds as Anti-fouling Biocides

To test the activity against growth on objects immersed in the sea, the compound according to Example 1 is incorporated into anti-fouling paints. An anti-fouling paint such as is known to the expert and which is based on vinyl chloride copolymer/rosin (2/1 part by weight) with a pigment volume concentration of about 40%, and a second anti-fouling paint of similar make-up but with a higher rosin content (vinyl chloride copolymer/rosin=1/1) are prepared. The compound according to Example 1 is incorporated into these paints, the paint is brushed onto specimen sheets and, after drying (10 days), the sheets are suspended in the North Sea. The corresponding paints but without adding of the product are exposed in the same way for comparison. On a rating scale of 0 (=completely covered with growth) to 10 (=completely free from growth), the following results are obtained after exposure for 6½ weeks (growth by hydroids=HY; growth by barnacles=BA):

Vinyl/rosin 2:1: without additive HY 5, BA 5
Vinyl/rosin 2:1: with additive HY 8, BA 8
Vinyl/rosin 1:1: without additive HY 0, BA 0
Vinyl/rosin 1:1: with additive HY 4, BA 10.

EXAMPLE 19

Use as an Algicide in Polymeric Material

To test the activity against attack by algae, various concentrations, which can be seen from Table 3, of the compound according to Example 1 are incorporated into roof sheeting consisting of polyisobutylene. A roof sheeting without biocide is investigated as a comparison.

A 1 cm$^2$ piece of film from each test strip is kept in water for 5 days, in each case placed on an algae agar plate and inoculated with 0.1 ml of a 1+1+1 mixture of 14-day cultures of the algae *Chlorella vulgaris* and *Chlorella spec.* (isolated from damage cases in practice) and *Scenedesmus obliques*, which had been diluted 1/10 in saline.

After 3 weeks, the plates are evaluated and the films are placed in fresh agar and inoculated again.

Evaluation of the growth after 3 and 6 weeks under artificial light is performed in accordance with the following scheme.

1 = growth on the film
2 = partial growth on the film
3 = growth up to the edge of the film
4 = inhibiting aerola around the film <5 mm
5 = inhibiting aerola around the film >5 mm The following result is obtained:

TABLE 3

| | | algae growth after | |
|---|---|---|---|
| | | 3 | 6 weeks |
| Film with addition of the compound according to Example 1 in % by weight | 0,1 | 4 | 4 |
| | 0,5 | 4 | 4 |
| | 1 | 4 | 4 |
| Comparison film without addition | | 2-3 | 2 |

EXAMPLE 20

Example 19 is repeated, except that instead of the stated concentrations of compound according to Example 1 alone, a combination of 1% by weight of the compound according to Example 1 and 0.07% by weight of 2-methylthio-4-t-butylamino-6-cyclopropylamino-s-triazine is used. The results obtained can be seen from Table 4.

TABLE 4

|  | algae growth after | |
|---|---|---|
|  | 3 | 6 weeks |
| Film with addition of 1% of the compound according to Example 1 + 0.07% of 2-methylthio-4-t-butylamino-6-cyclopropylamino-s-triazine | 5 | 5 |
| Comparison form without addition | 2-3 | 2 |

EXAMPLE 21

Use as a Fungicide in Wood

Determination of the limit of the activity against wood-destroying Basidiomycetes bred on agar (in accordance with EN 113). The test methods described in this European Standard is a laboratory method which forms a basis for evaluation of the activity of a wood preservative against wood-destroying Basidiomycetes. It allows determination of the limit concentration from which a susceptible type of wood can be regarded as being adequately protected after impregnation under the experimental conditions.

TEST FUNGI

The test fungi are listed below:
*Coniophora puteana* (Schumacher ex Fries) Karsten, strain FPRL 11E, for soft timbers=strain 91,
*Poria placenta* (Fries) Cooke sensu. J. Eriksson, strain SPRL 280, for soft timbers=strain 96,
*Gloeophyllum trabeum* (Persoon ex Fries) Murrill, strain BAM up to 109, for soft timbers=strain 94, Breeding of the strain and composition of the nutrient medium were as described in EN 113.

Solutions of isopropanol/water (1:1) containing 0.2%, 0.5%, 1%, 2% and 5% of active substance according to Example 1 are prepared.

The specimen woods of pine, nominal dimensions: 50 mm×25 mm×15 mm, are obtained and prepared as described in EN 113.

The impregnation according to EN 113 ensures complete thorough impregnation of the specimen woods with the wood preservative solution.

The amount of preservative absorbed is converted into weight per unit volume of the wood.

After impregnation the specimen woods are dried for 4 weeks, conditioned and, for sterilization, sterilized in films using electrons (beam energy 2.5 MeV, minimum dose 25 kGy).

The actual fungus experiment is carried out as described in EN 113 (duration of experiment 16 weeks).

At the end of the experiment, the specimen woods are removed from the experimental vessels and freed from adhering fungus mycelium.

The limit of the activity of a wood preservative is determined by the two amounts of wood preservative which correspond to
the lowest concentration which preserves the wood and
the next lowest concentration in the series, at which the wood is no longer adequately preserved.

The protection achieved by the wood preservative is regarded as being adequate for a given concentration if the mean corrected loss in weight of the specimen woods is less than 3% and
not more than one specimen wood shows a loss in weight of more than 3% but less than 5%.

The limit of the activity is given for each species of fungus by the limiting values in kg of preservative per m³ of wood. The corresponding concentrations of the preservative in the particular solvent or diluent are stated.

| Strain | No. | Effective concentration (%) | Take-up kg/m³ |
|---|---|---|---|
| *Coniophora puteana* FRRL 11 E | 91 | 0.5–1.0 | >3.0–<6.0 |
| *Poria placenta* FRRL 280 | 96 | 1.0–2.0 | >5.0–<10.0 |
| *Gleophyllum trabeum* BAM. EbW 109 | 94 | ≦0.2 | ≦1.0 |

As can be seen from the table, the active substance according to Example 1 is highly effective against the wood-destroying fungi investigated here.

What is claimed is:

1. A composition containing
a) paint and
b) at least one compound of the formula (I)

$$R^1{}_3Y^\oplus R^2 X^\ominus \qquad (I)$$

in which the radicals $R^1$ are identical or different and are $C_2$–$C_6$alkyl, phenyl, $C_1$–$C_2$alkyl-substituted phenyl or $C_5$–$C_7$cycloalkyl, benzyl, tolyl or hydroxy-$C_1$–$C_4$alkyl and $R^2$ is straight-chain or branched $C_8$–$C_{22}$alkyl, and Y is P and X is $BF_4$ or $PF_6$.

2. A composition according to claim 1 wherein X is $BF_4$.

3. A composition according to claim 1 wherein $R^2$ is $C_{10}$–$C_{16}$alkyl.

4. A composition according to claim 1 wherein $R^2$ is $C_{12}$–$C_{14}$alkyl.

5. A composition according to claim 1 wherein $R^1$ is n-butyl, $R^2$ is straight or branched chain $C_8$–$C_{22}$alkyl, Y is P and X is $BF_4$ or $PF_6$.

6. A composition according to claim 1 wherein said compound of formula (I) is $$(n\text{-}C_4H_9)_3P^\oplus(n\text{-}C_{14}H_{29})BF_4^\ominus \text{ or}$$

$$(n\text{-}C_4H_9)_3P^\oplus(n\text{-}C_{14}H_{29})PF_6^\ominus.$$

7. A composition containing
a) a polymeric material in the form of a building material and
b) at least one compound of the formula (I)

$$R^1 Y^\oplus R^2 X^\ominus \qquad (I)$$

in which the radicals $R^1$ are identical or different and are $C_2$–$C_6$alkyl, phenyl, $C_1$–$C_2$alkyl-substituted phenyl or $C_5$–$C_7$cycloalkyl, benzyl, tolyl or hydroxy-$C_1$–$C_4$alkyl and $R^2$ is straight-chain or branched $C_8$–$C_{22}$alkyl, and Y is P and X is $BF_4$ or $PF_6$.

* * * * *